United States Patent [19]

Potter et al.

[11] Patent Number: 5,128,243
[45] Date of Patent: Jul. 7, 1992

[54] ASSAY FOR THE DETECTION OF BEET SUGAR ADULTERATION OF FOOD PRODUCTS

[75] Inventors: Robert L. Potter; Richard L. L. Mansell, both of Tampa, Fla.

[73] Assignee: University of South Florida, Tampa, Fla.

[21] Appl. No.: 544,890

[22] Filed: Jun. 28, 1990

[51] Int. Cl.⁵ .................. G01N 33/53; G01N 33/537; G01N 33/543; A61K 35/14
[52] U.S. Cl. ................................ 435/7.92; 435/7.9; 530/389.1; 436/518; 436/815; 426/231
[58] Field of Search ............... 435/7.92, 7.9; 530/587; 436/540, 825, 518; 426/231

[56] References Cited

PUBLICATIONS

Doner et al., Chem. Abs. 107: 38149w, 1987.
Bricout et al., Chem. Abs 107: 132937y, 1987.
Maurer et al., Methods in Enzymology 70: 49–70, 1980.

*Primary Examiner*—Esther L. Kepplinger
*Assistant Examiner*—Donna C. Wortman
*Attorney, Agent, or Firm*—Sherman and Shalloway

[57] ABSTRACT

An immunoassay for the detection of beet sugar adulteration of sugar-containing materials such as fruit juices and fruit juice concentrates utilizes antibodies to proteinaceous components of beet sugar. These proteinaceous components have been found in all samples of beet sugar, tested, regardless of source or degree of refinement; these proteinaceous components have also been found in both crystal and invert sugars.

44 Claims, 2 Drawing Sheets

IMMUNOBLOT 1000x dil IgG          5000x dil IgG

FIG. 4

XTAL  LMW   XTAL  LMW   XTAL  LMW   XTAL  LMW

ASSAY FOR THE DETECTION OF BEET SUGAR ADULTERATION OF FOOD PRODUCTS

BACKGROUND OF THE INVENTION

1. Field of the Invention

The present invention relates to the detection of beet sugar in food products. More particularly, the present invention relates to an immunoassay directed to the detection of beet sugar in food products and a kit to effect such an immunoassay.

2. Description of the Prior Art

Beet sugar is a relatively pure, multi-use food composed almost totally of sucrose. Its sweetness and relative cost make it a useful additive to a number of commercially available food stuffs to enhance flavor and desirability.

Considering the purity of beet sugar, e.g., 99.96% (McGinnis, R. A., "Juice Purification" in Beet Sugar Technology, R. A. McGinnis Ed., Chapter 7, pp. 155-84 (1982)), and the fact that sucrose from beets is chemically identical to sucrose from apples and oranges, beet sugar has also been used as an adulterant of various food products, especially juices.

Adulteration of juice products creates an economic burden on producers who honestly, and with quality in mind, endeavor to produce the best product possible. Besides the competitive profit edge afforded adulterators, honest producers who purchase juice concentrates need a way of discerning adulterated juice from natural products so as not to be legally responsible for the purchase of adulterated material. However, as previously noted, the high purity of beet sugar and the inability to discriminate sucrose from beets from sucrose from other plant sources, such as apples and oranges, has rendered this a formidable task.

SUMMARY OF THE INVENTION

In order to develop an assay for the detection of beet sugar adulteration of food products, it was first necessary to determine what to look for in commercial sugar preparations and how to look for it. Since tremendous sensitivity and specificity can be achieved through the use of an immunoassay (Ishikawa, E., "Development And Clinical Application Of Sensitive Enzyme Immunoassay For Macromolecular Antigens—A Review", Clinical Biochemistry, 20, 375-385 (1987), efforts were directed toward the use of this methodology for the detection of some residue contained in beet sugar. By using antibodies that have been specifically prepared to recognize a material of interest and coupling these to an enzyme amplification system, one can generate an extremely specific and sensitive identification system or assay.

The first step therefore, in designing an immunoassay, is to identify and obtain, in pure form, an antigen (a substance which is recognized by an antibody) or set of antigens. Thus, it was necessary to identify some residue in the relatively pure commercial beet sugar that would be common to all types of the product and yet unique to beet sugar (or at least not detected in the natural food products, such as fruit juices, which were to be assayed.

In this regard, instances had been described where individuals were apparently allergic to beet sugar (Randolph et al., "Beet Sensitivity: Allergic Reactions From The Ingestion Of Beet Sugar (Sucrose) And Monosodium Glutamate Of Beet Origin", J. Lab. Clin. Med., 36, 407 (1950); Richter et al., "Anaphlactoid Reactions In Connection With Infusion Of Invert Sugar Solutions Are Due To Macromolecular Contaminants", Int. Archs. Allergy Appl. Immun., 50, 606 (1976)) and yet not allergic to the major component, sucrose. Analysis of such observations suggests that some component or components that co-purify with sucrose during the crystallization procedure, or that are added during processing, might be the basis for the observed sensitivity. One of these reports (Richter et al., supra) pointed to certain polysaccharide components as the immunogenic substance in some cases. Another report (Neill et al., "Serological Studies On Sugar. Reactions Of Antiserums Of Type II Pneumonococcus And Of Leuconostoc Mesenteroides With Cane And Beet Sugars And With Cane Juice", Am. J. Hy., 34, 65-78 (1941)) demonstrated that some sugar samples contained material that reacted with antibodies directed toward specific cell surface antigens of certain bacteria, i.e. Type 2 pneumonococcus and *Leuconostoc mesenteroides*. This suggested that some of these bacteria (which are extremely heat resistant when encysted) or materials resulting from them may be present as a residue in sugar.

Additionally, while using large amounts of sugar for macromolecule stabilization, there were observed residues from concentrates of purified sugar that appeared to be proteinaceous in nature. Since beet sugar is extracted from plant materials which contain protein, it was possible that some of the isolated protein could be of plant origin. Alternatively, this material could have arisen from bacteria associated with beets before or during sugar processing.

After many early studies probing commercial beet sugar for molecules which might fit these antigenic criteria, it was decided to pursue the isolation and characterization of certain proteins that appeared to be consistent components of processed sugar and to use these molecules for the development of an immunoassay.

Accordingly, it is an object of the present invention to provide a method for determining the presence of beet sugar in a food product, especially fruit juice.

It is a further object of the present invention to provide one or more antibodies having an affinity for proteinaceous material(s) characteristic of beet sugar.

It is a still further object of the present invention to provide a immunoassay for detecting the presence of beet sugar in a food product, especially fruit juice.

It is a yet further object of the present invention to provide a kit for performing an immunoassay for beet sugar.

These and other objects of the invention, as will become apparent hereinafter, have been attained by the provision of an antibody to a proteinaceous component of beet sugar, said proteinaceous component of beet sugar comprising at least one proteinaceous material, found in beet sugar, selected from the group consisting of those proteinaceous materials, found in beet sugar, having a molecular weight as determined by carrying out electrophoresis on said proteinaceous material and comparing its movement with that of marker proteins of known molecular weight, of about 61,000 daltons, about 45,000 daltons, about 39,000 daltons, about 36,000 daltons, about 30,000 daltons, about 27,000 daltons, about 21,000 daltons and about 16,000 daltons.

In a presently preferred embodiment of the invention, the antibody is to a proteinaceous component of beet sugar comprising a mixture of proteinaceous materials, found in beet sugar, having molecular weights of about 61,000 daltons, about 45,000 daltons, about 39,000 daltons, about 36,000 daltons, about 30,000 daltons, about 27,000 daltons, about 21,000 daltons and about 16,000 daltons.

In another aspect, the present invention provides a method of detecting the presence of beet sugar in a sugar-containing material, said method comprising:

treating a test sample of said sugar-containing material to selectively recover proteinaceous materials therefrom to form a protein test sample;

contacting said protein test sample with an antibody to a proteinaceous component of beet sugar; and detecting the formation of proteinaceous component/antibody complexes.

In a presently preferred embodiment of the invention, the treatment of said test sample to selectively recover proteinaceous materials therefrom comprises contacting said test sample with a weak anion exchange resin and then eluting the material adsorbed on said weak anion exchange resin to form an eluant.

In another aspect, the present invention provides a rabbit IgG to a proteinaceous component of beet sugar, said proteinaceous component of beet sugar comprising at least one proteinaceous material, found in beet sugar, selected from the group consisting of those proteinaceous materials, found in beet sugar, having a molecular weight, as determined by carrying out electrophoresis on said proteinaceous material and comparing its movement with that of marker proteins of known molecular weight, of about 61,00 daltons, about 45,00 daltons, about 39,000 daltons, about 36,000 daltons, about 30,000 daltons, about 27,000 daltons, about 21,000 daltons and about 16,000 daltons.

In a still further aspect, the present invention provides a test kit for the detection of beet sugar in a sugar-containing material comprising:

a predetermined quantity of a first mammalian IgG to a proteinaceous component of beet sugar, said proteinaceous component of beet sugar comprising at least one proteinaceous material, found in beet sugar, selected from the group consisting of those proteinaceous materials, found in beet sugar, having a molecular weight, as determined by carrying out electrophoresis on said proteinaceous material and comparing its movement with that of marker proteins of known molecular weight, of about 61,000daltons, about 45,000 daltons, about 39,000 daltons, about 36,000 daltons, about 30,000 daltons, about 27,000 daltons, about 21,000 daltons and about 16,000 daltons; and a predetermined quantity of labelled second mammalian anti-first mammal IgG.

In a presently preferred embodiment, the first mammalian IgG is rabbit IgG and the labelled second mammalian anti-first mammal IgG is a goat anti-rabbit IgG-alkaline phosphatase conjugate.

DETAILED DESCRIPTION OF THE INVENTION

The present invention is directed to the detection of beet sugar in sugar-containing materials such as fruit juices and fruit juice concentrates. Detection is achieved using an immunoassay based on the discovery of proteinaceous components of beet sugar, which are unique to beet sugar (or at least not detectable in natural fruit juices and concentrates thereof), which are antigenic in nature. These proteinaceous components of beet sugar have been found in varying amounts in all beet sugar samples tested to date, regardless of the source and degree of refinement or processing (e.g., in both crystal and invert forms). Based on electrophoretic analysis, more than 20 bands (each band corresponding to a different molecular weight proteinaceous material) have been found. Of these, the bands having molecular weights of about 61,000 daltons, 45,000 daltons, 39,000 daltons, 36,000 daltons, 30,000 daltons, 27,000 daltons, 21,000 daltons and 16,000 daltons appear to be quantitively predominant, and thus these materials or various combinations thereof are preferably used to generate antibodies for the immunoassay.

These proteinaceous components of beet sugar, when subjected to acid hydrolysis, yield more than about 50% by weight of amino acids, rich in alanine, serine, glycine and proline (each is present in an amount of at least about 9% by weight of the total amino acids).

The proteinaceous components of beet sugar may be used individually or in combination to produce antibodies by conventional immunization techniques. Typically, a mammal such as a mouse, rat, guinea pig, rabbit, dog, sheep, goat, donkey, cattle, horse or monkey, preferably rabbit, will be inoculated with the proteinaceous component of beet sugar as antigen, and subsequently blood and/or sera will be recovered from the mammal and immunoglobulins, preferably, IgG, recovered therefrom. Such techniques are well known, in themselves, in the art and do not form a part of the present invention. Similarly, known techniques for the production of monoclonal antibodies may also be utilized in the production of immunoglobulins for use in the present invention.

The novel immunoglobulins (antibodies) of the present invention may be used to assay for the presence of proteinaceous components unique to beet sugar in sugar-containing materials.

Typically, the sugar-containing material, preferably in the form of an aqueous sugar solution, is treated to remove proteinaceous components therefrom, e.g., by contact with a weak anion exchange resin such as diethylaminoethyl-silica (DEAE-silica) or polyethyleneimine (PEI)/silica. These proteinaceous components may then be eluted from the anion exchange column with a small amount of high ionic strength buffer (pH about 7.4).

This eluant, after washing with low ionic strength buffer, may then be brought into contact with the novel antibodies of the present invention and the formation of proteinaceous component/antibody complexes detected.

The detection of proteinaceous component/antibody complexes may be effected by any conventional technique, e.g., enzyme-linked immunosorbent assay (ELISA), etc.

If desired, prior to contact with the novel antibodies of the present invention, the eluant of the weak anion exchange resin may be further concentrated by known techniques, such as ultrafiltration and/or precipitation and centrifugation (care being taken to retain components having a molecular weight of about 10,000 daltons or more).

Additionally, prior to contact with the weak anion exchange resin, the aqueous sugar solution may be reduced in sugar content, e.g., by dialysis, so as to remove at least a major portion of the sugar present in the sample, e.g., at least about 80% by weight removal, preferably, at least about 85% by weight removal. Dialysis is typically carried out with a membrane material capable of allowing removal of components having a molecular weight of not more than about 6,000 daltons.

Prior to dialysis and/or ion exchange, the aqueous solution may be filtered to remove any particulate material therein, e.g., bacteria, by filtration through a filter having a pore size of less than about 0.5 micron, preferably about 0.2 micron.

In order to effectuate the immunoassay of the present invention, the novel antibodies of the present invention may be provided in a kit along with other materials conventionally utilized in immunoassays. For example, a predetermined quantity of a first mammalian IgG to a proteinaceous component of beet sugar (e.g., rabbit anti-beet IgG) and a predetermined quantity of a labelled second mammalian anti-first mammalian IgG (e.g., goat anti-rabbit IgG-alkaline phosphatase conjugate) may be packaged together, or along with other conventional components for the conduct of various immunoassays, e.g., buffers, multi-well plates, polyacrylamide gel slabs, Immobilon ® AV sheets, sodium dodecyl sulfate, etc. Suitably, a standard unadulterated sample of material being assayed, e.g. apple juice, orange juice, etc., may also be included.

Since the present ELISA technique of the inventive immunoassay can detect quantities of the proteinaceous components of beet sugar on the order of 25-50 ng, and since the amount of proteinaceous components found in beet sugars is variable with the degree of processing and/or refinement, and since the degree of adulteration may vary, care must be taken in sample size selection to ensure recovery of the minimum detectable amounts of proteinaceous components of beet sugar, if adulterants are present.

EXAMPLE 1

Isolation Of Proteins From Commercial Beet Sugar Preparations

Sugar Samples and Reagents

Crystalline sugar was purchased from Spreckels Sugar Co., both the Woodland, Calif. and Pleasanton, Calif. facilities; as well as from Amalgamated Sugar Co., Nampa, Id. and Oak Grove, Ill. European Crystal came from Weiss Zuckfer EG Qualitaet II Fuellgewicht Zuckerfabrik Juelich AG, West Germany and Fa. Steirobst GesmbH. Austria. Inverted sugar samples came from Spreckels Sugar Co., Sudzucker AG, West German and Tree Top Apples, Inc. All other chemicals used were reagent grade with sodium azide, thiourea, ammonium bicarbonate and sodium phosphate purchased from Fischer Scientific, Fairlawn, N.J. Mercaptoethanol was obtained from Sigma Chemical Co., St. Louis, Mo.

Protein Isolation

Beet sugar proteins were isolated as follows. Beet sugar, from various commercial sources, was prepared as a 15° Brix solution in aqueous medium A (0.1% sodium azide, 5 mM thiourea, and 2 mM $\beta$-mercaptoethanol). Following vacuum filtration through a 0.45 $\mu$m Supor 450 membrane filter (Gelman Sciences), the sugar solution was dialyzed by counter current dialysis using three Spectra/Por RC Hollow Fiber bundles (Molecular Weight Cut-Off 6000) linked in series. The dialyzing medium was identical to medium A.

Following dialysis, 4 liters of the approximately 2° Brix sugar solutions were loaded at 4° C. onto each of five small anion exchange columns (1 mL bed vol. PEI/silica SPE-10 J. T. Baker Chemical Co.}. Material was eluted at room temperature with 2.5 column volumes of aqueous 550 mM ammonium bicarbonate (pH 7.8) and the resulting eluate from 5 columns was combined and concentrated as described below. The samples at this stage were characterized by a light straw to dark golden yellow color.

Protein Concentration

The column eluant was reduced under pressurized nitrogen gas (30 PSI) to 2 ml volume using Novacell NMWL 10000 (Molecular Weight Cut-Off 10,000}Stirred Pressure Cell (Filtron Technology Corp.). The retentate was further concentrated and desalted by a series of centrifugations at 5000 rpm in a Centricon 10000 MWCO (Molecular Weight Cut-Off) Microconcentrator (Amicon Division, W. R. Grace Co.). Following each spin, the retentate was diluted to double volume by addition of an aqueous 0.1% sodium azide and 2 mM $\beta$-mercaptoethanol solution and reconcentrated. This process was repeated six times.

Protein Determination

Protein concentration was determined by the Coomassie Blue dye binding assay (Bradford, M., "A Rapid And Sensitive Method For The Quantification Of Microgram Quantities Of Protein Utilizing The Principle Of Protein Dye Binding", Anal. Biochem., 72, pp. 248-254 (1976)). using the Bio-Rad Protein Assay Kit 1 (Bio-Rad Laboratories). Bovine plasma gamma globulin (Bio-Rad Laboratories) was used as the protein standard.

Protease Treatment

Samples were treated with papaya protease (Sigma Chemical Co.) 50:1, weight:weight, at either 4° C. or room temperature for 19 minutes. The reaction was terminated by the addition of sodium dodecyl sulfate (SDS) followed immediately by boiling for 2 minutes.

Polyacrylamide Gel Electrophoresis

Beet sugar proteins were fixed (2:1) in aqueous SDS denaturing solution (2.5% mM mercaptoethanol) and the resulting protein samples were separated on a 1 mm 10% acrylamide gel prepared as described by Laemmli, U. K., "Cleavage Of The Structural Proteins Of The Bacteriophage T-4", Nature (London), 227, pp. 680-685 (1970). Gels were run at room temperature with a constant current of 10 mA.

Protein molecular weights were estimated by the method of Weber et al., "The Reliability Of Molecular Weight Determinations By Dodecyl Sulfate-Polyacrylamide Gel Electrophoresis", J. Biol. Chem., 244, 4406 (1969) using molecular weight standards from Bio-Rad Laboratories, including phosphorylase b (97,400 daltons), bovine serum albumin (66,200 daltons), ovalbumin (42,700 daltons), carbonic anhydrase (31,000 daltons), soybean trypsin inhibitor (21,500 daltons), and lysozyme (14,400 daltons).

Gels were fixed in 10% isopropanol, 5% acetic acid for 10 minutes and stained in the same solution with 2.5% Coomassie Blue R-250. Destaining took place in 10% isopropanol, 5% acetic acid plus 3% glycerol. Gels were placed onto Whatman 3 mm paper and dried under vacuum.

Amino Acid Analysis

Samples were hydrolyzed in duplicate for 24 hours at 110° C. in 6N HCl, then the acid was removed by rotary evaporation. Amino acids were quantitated after derivatization with phenylisothiocyanate and separated by reverse phase high performance liquid chromatography (Heinrikson et al., "Amino Acid Analysis By Reverse-Phase High-Performance Liquid Chromatography: Precolumn Derivatization With Phenylisothiocyanate", Anal. Biochem., 136, 65–74 (1984)). The protein angiogenin was used as the standard for quantitation.

Figure 1:
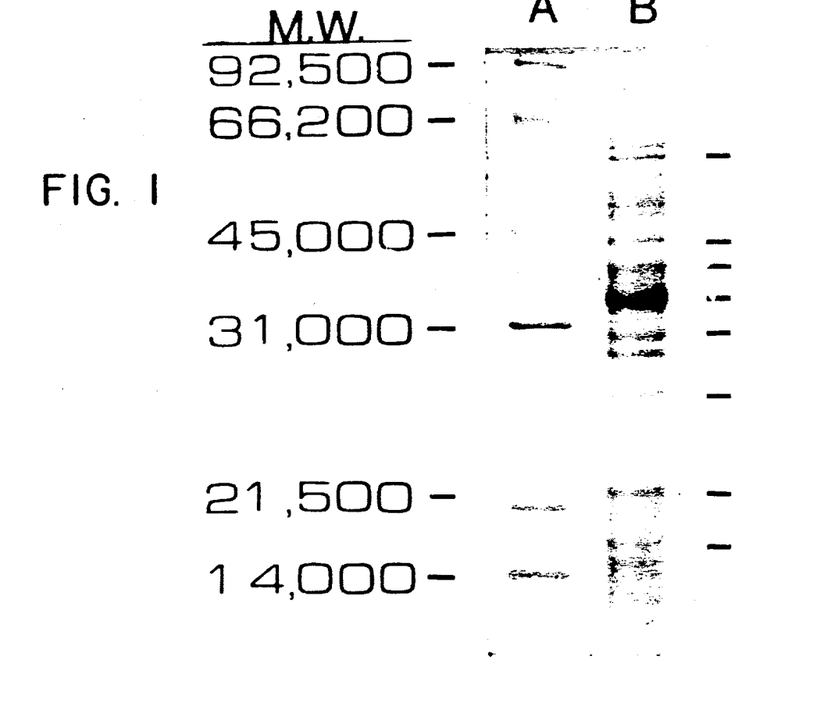
FIG. 1 is an electrophoretic profile of a crystal beet sugar protein extract (Coomassie Blue stained sodium dodecyl sulfate (SDS)-10% polyacrylamide gel (PAG)).

Using the aforementioned procedures, a protein containing fraction was isolated from a variety of commercially available beet sugar preparations (more than 12). The isolation procedure, as noted above, included a flow-through dialysis step to lower the sucrose concentration followed by chromatography on a weak anion exchanger. The final preparation was obtained by batch elution from the ion exchange column followed by concentration and washing of the eluted sample via ultrafiltration. The resulting, slightly yellow sample was analyzed by polyacrylamide gel electrophoresis and Coomassie Blue dye staining. A typical profile can be seen in FIG. 1, wherein lane A is a low molecular weight marker with molecular weights on the left and lane B is 9 µg of protein extract from crystal beet sugar (Amalgamated Sugar Co.). Major protein bands in the extract are indicated by hatch marks on the right. Estimated molecular weights (top to bottom) are 61,000 daltons (doublet), 45,000 daltons, 39,000 daltons, 36,000 daltons, 30,000 daltons (doublet), 27,000 daltons, 21,000 daltons, and 16,000 daltons. More than 20 Coomassie Blue staining bands can be seen with prominent bands at 61,000, 45,000, 36,000, 30,000, 27,000, and 20,000 daltons.

Figure 2:
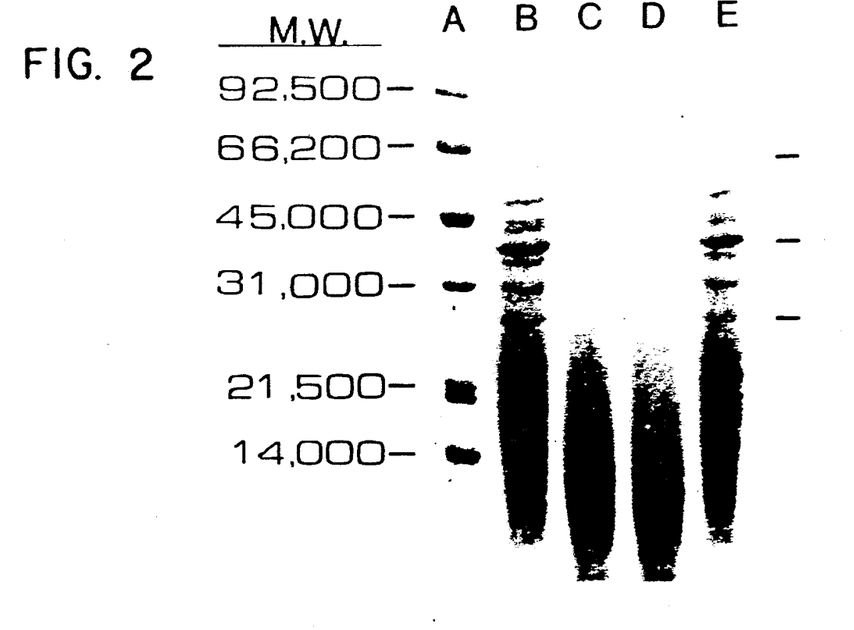
FIG. 2 is an electrophoretic analysis of protease-treated and-untreated crystal beet sugar protein extract (Coomassie Blue stained SDS-PAG).

The proteinaceous characteristics of this staining material can be inferred from the experiments shown in FIG. 2 and from Table 1. As shown in FIG. 2, when the protein samples were exposed to a mixture of papaya protease prior to electrophoresis, the stained bands were no longer seen but were replaced by a heavy, diffuse staining around the dye front. In particular, lane A is a low molecular weight marker with molecular weights on the left. Lane B is 12.6 µg of untreated protein extract incubated at room temperature. Lane C is 12.6 µg of protease-treated protein extract incubated at room temperature. Lane D is 12.6 µg of protease-treated protein extract incubated at 4° C. Lane E is 12.6 µg of untreated protein extract incubated at 4° C. Major protein bands in the extract are indicated by hatch marks on the right. Estimated molecular weights (top to bottom) are 61,000 daltons (doublet), 36,000 daltons and 27,000 daltons.

Amino acid analysis of the isolated material, as shown in Table 1, also indicated the presence of macromolecular polymers of amino acids linked by acid labile bonds. Greater than 50% of the mass of the material could be recovered as standard protein amino acids (36µg of amino acids from 66 µg starting material). Several other unidentified peaks were also evident in the analysis profile and may account for some of the remaining mass. Evidence does exist to indicate that glycoproteins are involved here since the bands of proteinaceous material separated by SDS-PAGE also test positive for carbohydrates.

The amino acid profile would seem to indicate proteins rich in alanine, serine, glycine and, interestingly, relatively rich in proline.

TABLE 1

Amino Acid Analysis of Protein Extract From Crystal Beet Sugar (Amalgamated Sugar Co.).

| Amino Acid | Mole Percent | |
|---|---|---|
| | Sample 1 | Sample 2 |
| Asp | 7.9 | 8.8 |
| Glu | 6.4 | 6.6 |
| Ser | 10.4 | 11.3 |
| Gly | 10.2 | 13.0 |
| His | 1.3 | 1.2 |
| Arg | 1.8 | 1.6 |
| Thr | 6.6 | 6.4 |
| Ala | 14.0 | 14.1 |
| Pro | 9.6 | 9.0 |
| Tyr | 3.0 | 2.8 |
| Val | 7.3 | 6.4 |
| Met | 2.3 | 2.2 |
| Ile | 4.3 | 4.2 |
| Leu | 7.8 | 6.2 |
| Phe | 3.6 | 3.2 |
| Lys | 3.5 | 3.2 |

Figure 3:
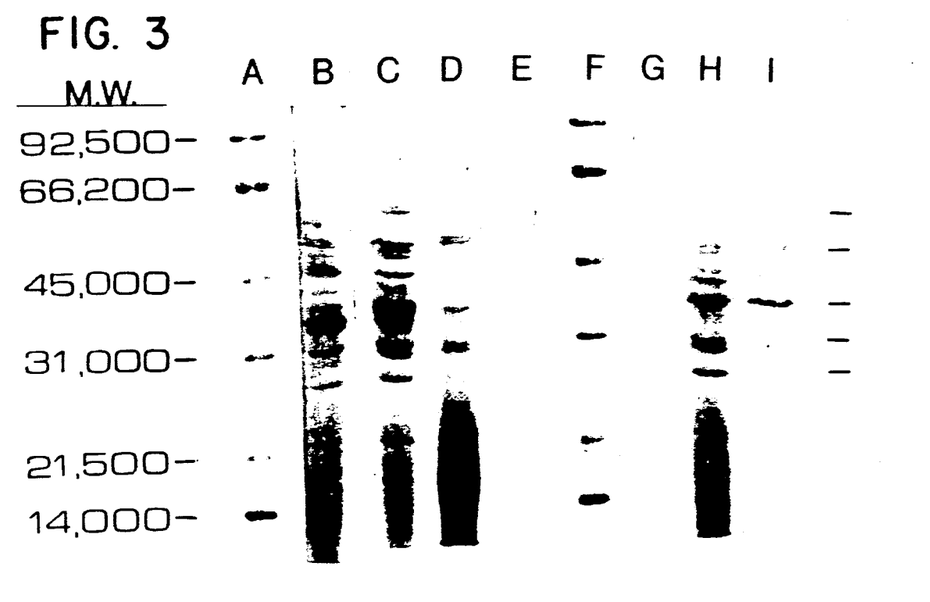
FIG. 3 represents electrophoretic profiles of protein extracts from various crystal and invert beet sugars (Coomassie Blue stained SDS-PAG).

The similarity of proteins isolated from different sugar sources can be seen in FIG. 3 which shows an electrophoretic comparison of material isolated from several different sugar products. Samples from each source have been isolated a minimum of 3 times with identical results to those illustrated. Lanes B-D are invert sugar samples from Spreckels Sugar Co. in California (invert sugar means some proportion of the sucrose has been hydrolyzed to fructose and glucose), and lanes G-I are three different crystal sugar samples, including one from Austria (lane G). More particularly, lanes A and F are low molecular weight marker with weights on the left. Lane B is 13 µg of protein extract from 50% invert. Lane C is 24 µg of protein extract from 78% invert. Lane D is 30 µg of protein extract from 90% invert. Lane E is a blank. Lane G is 15 µg of protein extract from crystal (Austria) Lane H is 37 µg of protein extract from medium grade crystal (Amalgamated Sugar Co., USA). Lane I is 7 µg of protein extract from highly refined liquor grade crystal (Spreckels Sugar Co., USA). Major protein bands in the protein extracts are indicated by hatch marks on the right. Estimated molecular weights (top to bottom) are 61,000 daltons (doublet), 45,000 daltons, 36,000 daltons, 30,000 daltons (doublet) and 27,000 daltons. Note that all of these samples show overlapping patterns of protein which in some cases look almost identical. The major protein bands evident in FIG. 1 can also be clearly seen in these samples. The few differences evident may simply reflect differences in how they are produced and is most clearly seen in FIG. 3. While most of the invert sugar protein bands (FIG. 3, lanes B-D) appear to be similar to those isolated from crystal sugar, the predominant band in these inverted samples appears to be one at 30,000 daltons along with lesser quantities of the usually dominant 36,000 daltons protein seen in the pattern from crystal (FIG. 3, lanes G-I). Thus, while some inverts do differ, they still show overlapping protein patterns and all sugar samples possess a protein band of about 30,000 daltons among others.

As with the protein profiles, yields of protein varied with the are of origin and also with the type and purity of the specific commercial samples used. Typical yields can be seen in Table 2 and are the average of at least 3 isolations. Crystalline samples contained the highest amounts of protein (about 700 to 1200 ng/g) whereas more highly purified or treated sugars such as liqueur grade or invert samples, contained the least about (50-350 ng/g).

TABLE 2

Protein Yields From Beet Sugars of Various Types and Sources.

| Type | *Yield/g Sugar | Source |
| --- | --- | --- |
| Crystal | 1226 ng ± 495 ng | White Satin Brand #12N110100H Amalgamated Sugar Co., Nampa, ID |
| Crystal | 760 ng ± 248 ng | White Satin Brand #12N07G704H Amalgamated Sugar Co., Nampa, ID |
| Crystal | 685 ng ± 149 ng | Spreckels MXR Spreckels Sugar Co. Pleasantville, CA |
| Crystal | 54 ng ± | Amstar Brand |
| Highly Ref. | 10 ng | Spreckels Sugar Co. Pleasantville, CA |
| Crystal European | 105 ng** | Weiss Zuckfer EG-Qualitat II, Fullgewicht Zuckerfabrik Julich AG, West Germany |
| 50% Invert | 566 ng ± 100 ng | Amalgamated Sugar Co. Oak Grove, IL |
| 50% Invert | 163 ng ± 112 ng | Spreckels Sugar Co. Woodland, CA |
| 67% Invert European | 43 ng ± 2 ng | Sudzuker AG West Germany |
| 78% Invert | 477 ng ± 170 ng | Amalgamated Sugar Co. Oak Grove, IL |
| 90% Invert | 158 ng** | Amalgamated Sugar Co. Oak Grove, IL |
| 90% Invert | 285 ng ± 56 ng | Spreckels Sugar Co. Woodland, CA |

*Protein concentrations determined by Bradford Protein assay
**Single Sample

Thus, there is evidence for the existence of discrete proteinaceous substances that can be purified from commercial beet sugar preparations. These proteins have been isolated from a number of domestic crystalline beet sugar samples, as well as from European beet sugar and domestic inverted samples.

The protein character of the isolated material was established in two ways. The material was susceptible to protease treatment, as shown by the loss of discrete Coomassie Blue staining bands on polyacrylamide gels. The material also yielded amino acids following vigorous acid hydrolysis. The amount of free amino acids liberated was consistent with these building blocks accounting for the major portion of the isolated material. During the amino acid analysis several unidentified peaks were also seen and may represent amino acids which were chemically altered during the rather harsh beet sugar extraction and purification procedure (Ebell et al., "Diffusion" in Beet Sugar Technology, R. A. McGinnis Ed., Chapter 6, pp. 119-132 (1982); McGinnis, R. A., "Juice Purification" in Beet Sugar Technology, R. A. McGinnis Ed., Chapter 7, pp. 155-184 (1982)). These peaks were not calculated in the amino acid recovery and could, if they are modified amino acids, add to the 54% recovery. Furthermore, the initial quantitation of protein is based on the Coomassie Blue dye binding method of Bradford which is known to vary for different proteins (Davis, E. M., "Protein Assays: A Review Of Common Techniques", Biotechnology Laboratory, 6(5), pp. 28-37 (1988)). The actual amount of protein hydrolyzed could have been overestimated if some portion of the isolated material is not protein but interferes with the dye binding assay. Certain flavonoid substances for instance are known to do this, thereby giving elevated protein values (Compton et al., "Mechanism Of Dye Response And Interference In The Bradford Protein Assay", Anal. Biochem., 151, pp. 369-374 (1985)). In terms of the amino acid makeup, since the analysis is derived from a mixture of proteins, the interpretations are limited, however, the relatively high amount of serine and threonine (about 16%) is consistent with the type of amino acids which could interact with the hydrogen bonding potential of sucrose.

The amounts of protein found in different crystal preparations were small, but consistent, from batch to batch ranging from about 1200 ng/g sugar to about 50 ng/gram sugar depending on the producer. Highly refined liqueur grade sucrose appears to have less total protein which is probably due to the increased number of purification steps required to obtain this product. The refined sugar still contains the same major protein bands as seen in the other samples (61,000, 45,000, 36,000, 30,000, and 27,000 daltons). Thus, while the total amount of protein per gram of sample seems to change from producer to producer and with the amount of processing, the qualitative pattern remains remarkably similar.

It is interesting to note that some of the invert sugar samples show a decreased amount of the protein band at 36,000 daltons and a relative increase in the protein band at 30,000 daltons. Since invert sugar (sugar which has had some sucrose hydrolyzed to fructose and glucose) is produced by more than one method (Gaddie, R. S., "Liquid Sugars" in Beet Sugar Technology, R. A. McGinnis, Ed., Chapter 15, pp. 537-544 (1982)), these differences may simply reflect the different sugar processing procedures. Most invert production involves treatment of sucrose solutions with mild HCl for varying lengths of time and at various temperatures. Thus, the differences in the profiles of the proteins isolated from the sugars processed by the various methods might be explained by selective hydrolysis or differential precipitation of certain proteins that change as a result of the procedure used for inversion. For instance, selective hydrolysis at certain, more susceptible amide bonds (i.e., Aspartic Acid-Proline (Laursen, R. A., "Automatic Solid Phase Edman Degradation", Methods In Enz., 25, 344 (1977); Allen, G., "Sequencing Of Proteins And Peptides", Lab Tech. Biochem. Mol. Biol., 9, 50 (1981)) could lead to loss of one or more larger proteins with concomitant increases in one or more smaller ones. This possibility is enhanced by the large percentage of proline and potential aspartic acid residues found in these proteins. Alternatively, the changed protein profile could be due to preferential loss of the 36,000 dalton protein during the acid treatment via denaturation and precipitation. In any case, several proteins of similar molecular weight can be isolated from both the inverted and regular sugar samples.

Since protein was found in all sugar samples tested, it was important to demonstrate that the protein material was a consistent component of the sugar samples and not endogenously produced during the isolation procedure. Several lines of evidence support this conclusion. First, all samples were maintained in 0.1% sodium azide which is known to be an effective inhibitor of aerobic bacterial growth. Second, an equivalent portion of buffer, in which the sugar is normally dissolved, failed to show any Coomassie or silver staining bands on SDS-PAGE when processed through the described procedure. Third, the same protein bands can be obtained by passing the 15° Brix solution directly through ion exchange columns without a dialysis step (data not shown). While the yields of the proteins are reduced, possibly due to the elevated sucrose interfering with binding, the fact that they can still be found suggests they are not generated in situ. The nonbinding protein can also be recovered if this fraction is dialyzed and concentrated and the resulting protein profile appears similar to that seen for the initial sample (data not shown). Finally, the fact that some acid inverted sugar extracts show a different quantitative pattern of proteins on SDS-PAGE than crystalline extracts strongly supports the idea that these proteins are specifically associated with the commercial sugar preparations and are not being generated during the isolation procedure.

While the existence of small amounts of specific proteins in all of the commercial beet sugar preparations tested has been established, the origin of these macromolecules remains unknown. Since these proteins are found in sugars from such diverse areas as California, Utah, Germany and Austria, the most likely candidate source would seem to be the beet plant material, although contamination of beets or beet sugar with specific microorganisms (Halden, H. E., revised by Bolinder, M., "Microbiology and Plant Sanitation" in Beet Sugar Technology, R. A. McGinnis, Ed., Chapter 23, pp. 723-740 (1982)) cannot be ruled out.

EXAMPLE 2

Production of Antibodies and Use of Same in an Immunoassay

Antibody Production

Two young female rabbits were injected with 500μg each, of antigen, as obtained in Example 1, in complete Freunds adjuvant (final volume 400μl). Injections continued for a total of 4 weekly injections. The animals were rested one week and then boosted with 50-500 μg antigen per rabbit. The animals were bled from an ear vein the next 2 weeks with approximately 20-25 ml being obtained each time. This cycle of boost, rest, bleed, bleed was continued for 9 months.

Antibody Purification

Non-immune and immune IgG antibody fractions were isolated from the serum by precipitation in a 30-50% saturated ammonium sulfate (Goding, J. W., "Monoclonal Antibodies: Principals and Practice", Academic Press, Inc., Orlando, Fla. (1983), pp 114-115). The precipitate was dialyzed overnight at 4° C. against 2-3 changes of 10 mM Tris-HCl (pH 8.0) to remove salts. Following dialysis, the IgG fraction was dried by lyophilization and stored at 4° C.

The non-immune and immune IgG fractions were prepared as 1 mg/ml TBS (20 mM Tris, 150 mM NaCl, pH 7.5) stock solutions and stored at −20° C. until needed.

Immunoblotting

After separation by sodium dodecyl sulfate-polyacrylamide gel electrophoresis (SDS-PAGE), as described in Example 1, proteins were electroblotted (Towbin, et al., Proc. Nat. Acad. Sci. USA, 76, 4350 (1979); Lin, et al., "On the Electrotransfer of Polypeptides from Polyacrylamide Gels to Nitrocellulose Membranes", Anal. Biochem., 128, 302 (1982) from the gel onto an Immobilon-PVDF (polyvinylidene difluoride) transfer membrane (Millipore Corp.). The PVDF transfer membrane was pre-wet with methanol, washed in distilled water for 5 minutes and soaked in transfer buffer for at least 30 minutes prior to electroblotting. The polyacrylamide gel was also pre-equilibrated in transfer buffer at room temperature. Two changes of transfer buffer over 35 minutes was used to remove the SDS.

Protein transfer to the solid-phase membrane was done using a Genie Electroblotter (Idea Scientific) for 1 hour at 4° C. and 10 volts in a medium consisting of 80% tris/glycine buffer (25 mM Tris, 192 mM Glycine pH 8.3), 20% methanol.

Dot Blotting

Protein was applied to a solid phase surface essentially as described by Towbin, et al. "Immunoblotting and Dot Immunoblotting-Current Status and Outlook", J. Immuno. Methods, 72, 313-340 (1984).

Antigen Detection

Following electrotransfer or dot blotting of the proteins, unbound membrane sites were blocked with a 3% solution of gelatin in TBS (20 mM Tris, 150 mM NaCl, pH 7.5) for 1 hour at 37° C. on a rotary shaker. Unbound gelatin was removed by three 5-minute washes with 0.1% gelatin in TBS.

Protein bound to the transfer membrane was then exposed to antibody diluted in 1% gelatin, 0.02% RIA grade "Tween-20" (Bio-Rad Laboratories) and incubated in TBS at room temperature on a rotary shaker for 1 hour to overnight depending on the study. Unbound antibody was removed from the transfer membrane by three 5-minute washes of 0.1% gelatin in TBS. Protein antibody conjugates were visualized by enzyme linked immuno-assay by incubation with 1000 x dilution of Goat anti-Rabbit IgG Alkaline Phosphatase Conjugate (Sigma Chemical Co.) in 1.0% gelatin, 0.02% EIA grade "Tween-20" (Bio-Rad Laboratories) in TBS for 1 hour at room temperature on a rotary shaker. Unbound antibody was removed as described above.

Color development was achieved by incubating at 37° C. in alkaline phosphatase substrate until the desired level of color development had occurred. The reaction was stopped by rinsing the transfer membrane in distilled water and allowing to air dry. The alkaline phosphatase substrate consisted of 5 ml 0.1% nitro blue tetrazolium (Sigma Chemical Co.) in 0.1 M Tris pH 9.6, 0.5% 5-bromo-4-chloro-3-indolyl phosphate (Sigma Chemical Co.), 45 ml 0.1M Tris pH 9.6, 0.2 ml 1M MgCl$_2$.

Figure 4:
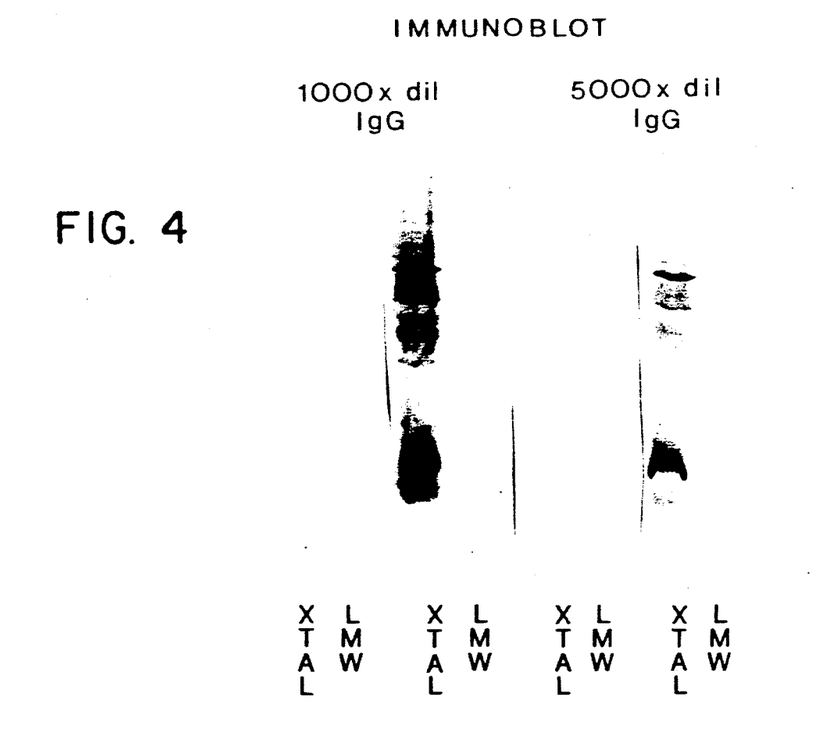
FIG. 4 is a Western Blot comparison of rabbit nonimmune and anti-beet protein IgG reactivity to crystal beet sugar protein extract wherein the protein extracts had been separated by SDS-PAG electrophoresis (SDS-PAGE) followed by electrotransfer to solid phase membrane.

The specificity of the antibody preparation for the isolated protein can be seen in FIG. 4, which shows a Western blot analysis of the isolated proteins comparing immune and non-immune antibody preparations, wherein XTAL is 55 μg of protein extract from Crystal (Amalgamated Sugar Co.) and LMW is low molecular weight marker. In particular, FIG. 4 reads from left to right: 1000 x dilution of Rabbit non-immune antibodies; 1000 x dilution of Rabbit anti-beet protein antibodies; 5000 x dilution of Rabbit non-immune antibodies; and 5000 x dilution of Rabbit anti-beet protein antibodies. The non-immune preparation shows very little interaction with the specific proteins while the immune antibody preparation shows a very strong interaction. This result implies that there are a number of antibodies present in the immune preparation that specifically interact with the isolated protein and that these same antibodies are not present in the non-immune or control preparation. The antibodies also appear to have a relatively high avidity for the proteins as evidenced by the strong antibody-protein interaction at low antibody concentrations (200 ng/ml) and by the fact that these interactions withstand quite stringent washing conditions.

The ability to detect beet sugar in apple juice was then tested. Samples (certified unadulterated) were spiked with sugar (Amalgamated Crystal) to the levels of 2%, 5%, 10% and 20% weight/vol. Samples were prepared and concentrated, with the indicated aliquots being subjected to immunoassay by dot blot analysis. The results of this experiment for buffer and apply juice look quite similar when small aliquots of each are used. This implies that apply juice itself, like simple salt buffer, has very little interaction with the antibodies although some small color reaction can be seen when large amounts (100 mls) of sample are used. More importantly, there is a marked increase in color yield with increasing amounts of adulteration. These samples clearly appear darker, indicative of increased reactions with antibody. This experiment then, demonstrated that apple juice has very little reactivity with the antibodies, and samples that have been adulterated with crystal beet sugar could be identified in comparison to non adulterated samples.

To further validate these results, a blind experiment was set up. Ten samples of apple juice that had been adulterated with invert sugar in concentrations ranging from 0 to 25% were prepared. These were tested with the assay. It was possible to order the levels of adulteration (from least to greatest) which were subsequently confirmed by the preparers. Most easily identified are the heavily adulterated samples and the unadulterated samples. With these results and a similar one for adulterated orange juice, a workable assay for beet sugar adulteration of juice has been achieved.

What is claimed is:

1. An antibody raised against a proteinaceous component of beet sugar, said proteinaceous component of beet sugar comprising at least one proteinaceous material, found in beet sugar, selected from the group consisting of those proteinaceous materials, found in beet sugar, having a molecular weight as determined by carrying our electrophoresis on said proteinaceous material and comparing its mobility with that of marker proteins of known molecular weight, of about 61,000 daltons, about 45,000 daltons, about 39,000 daltons, about 36,000 daltons, about 30,000 daltons, about 27,000 daltons, about 21,000 daltons, and about 16,000 daltons.

2. The antibody according to claim 1, wherein said proteinaceous component of beet sugar comprises more than about 50% by weight of amino acids linked by acid labile bonds.

3. The antibody according to claim 2, wherein said proteinaceous component is rich in alanine, serine, glycine and proline.

4. The antibody according to claim 2, wherein said proteinaceous component of beet sugar comprises a proteinaceous material, found in beet sugar, having a molecular weight of about 61,000 daltons.

5. The antibody according to claim 2, wherein said proteinaceous component of beet sugar comprises a proteinaceous material, found in beet sugar, having a molecular weight of about 45,000 daltons.

6. The antibody according to claim 2, wherein said proteinaceous component of beet sugar comprises a proteinaceous material, found in beet sugar, having a molecular weight of about 39,000 daltons.

7. The antibody according to claim 2, wherein said proteinaceous component of beet sugar comprises a proteinaceous material, found in beet sugar, having a molecular weight of about 36,000 daltons.

8. The antibody according to claim 2, wherein said proteinaceous component of beet sugar comprises a proteinaceous material, found in beet sugar, having a molecular weight of about 30,000 daltons.

9. The antibody according to claim 2, wherein said proteinaceous component of beet sugar comprises a proteinaceous material, found in beet sugar, having a molecular weight of about 27,000 daltons.

10. The antibody according to claim 2, wherein said proteinaceous component of beet sugar comprises a proteinaceous material, found in beet sugar, having a molecular weight of about 21,000 daltons.

11. The antibody according to claim 2, wherein said proteinaceous component of beet sugar comprises a proteinaceous material, found in beet sugar, having a molecular weight of about 16,000 daltons.

12. The antibody according to claim 2, wherein said proteinaceous component of beet sugar comprises a mixture of proteinaceous materials, found in beet sugar, having molecular weights of about 61,000 daltons, about 45,000 daltons, about 39,000 daltons, about 36,000 daltons, about 30,000 daltons, about 27,000 daltons, about 21,000 daltons and about 16,000 daltons.

13. The antibody according to claim 1, wherein said beet sugar is a crystalline sugar.

14. The antibody according to claim 1, wherein said beet sugar is at least partially inverted.

15. The antibody according to claim 14, wherein said at least partially inverted beet sugar has a degree of inversion of about 50 to 90%.

16. A method of detecting the presence of beet sugar in a sugar-containing material, said method comprising:
    treating a test sample of said sugar-containing material to selectively recover proteinaceous materials therefrom to form a protein test sample;
    contacting said protein test sample with antibody raised against a proteinaceous component of beet sugar; and
    detecting the formation of complexes of said proteinaceous component and antibody.

17. The method of claim 16, wherein said treatment of said test sample to selectively recover proteinaceous materials therefrom comprises contacting said test sample with a weak anion exchange resin and then eluting the material absorbed on said weak anion exchange resin to form an eluant.

18. The method of claim 17, further comprising ultrafiltration of said eluant to produce a retentate.

19. The method of claim 18, wherein said ultrafiltration produces a retentate containing materials having a molecular weight of greater than about 10,000 daltons.

20. The method of claim 18, further comprising concentration of said retentate by centrifugation.

21. The method of claim 16, wherein said proteinaceous component of beet sugar comprises at least one proteinaceous material, found in beet sugar, selected from the group consisting of those proteinaceous materials, found in beet sugar, having a molecular weight, as determined by carrying out electrophoresis on said proteinaceous material and comparing its movement with that of marker proteins of known molecular weight, of about 61,000 daltons, about 45,000 daltons, about 39,000 daltons, about 36,000 daltons, about 30,000 daltons, about 27,000 daltons, about 21,000 daltons and about 16,000 daltons.

22. The method of claim 21, wherein said proteinaceous component of beet sugar comprises more than about 50% by weight of amino acids linked by acid labile bonds.

23. The method of claim 22, wherein said proteinaceous component is rich in alanine, serine, glycine and proline.

24. The method of claim 21, wherein said proteinaceous component of beet sugar comprises a mixture of proteinaceous materials, found in beet sugar, having molecular weights of about 61,000 daltons, about 45,000 daltons, about 39,000 daltons, about 36,000 daltons, about 30,000 daltons, about 27,000 daltons, about 21,000 daltons and about 16,000 daltons.

25. The method of claim 16, wherein said detection of said complexes is effected by enzyme-linked immunosorbent assay.

26. The method of claim 16, further comprising removing at least a major portion of the sugar present in a sample of said sugar-containing material to form said test sample.

27. The method of claim 26, wherein at least 80% of the sugar present in said sample of sugar-containing material is removed from said test sample.

28. The method of claim 27, wherein at least 85% of the sugar present in said sample of sugar-containing material is removed to form said test sample.

29. The method of claim 16, wherein said removal of said sample of said sugar-containing material is effected by dialysis.

30. The method of claim 29, wherein said dialysis removes materials having a molecular weight of not more than about 6,000 daltons.

31. The method of claim 26, further comprising forming an aqueous sugar solution of said sugar-containing material prior to removal of said major portion of the sugar therefrom.

32. The method of claim 31, wherein said aqueous sugar solution is filtered to remove particulate material therefrom prior to removal of said major portion of the sugar therefrom.

33. The method of claim 32, wherein said filtration removes particulate material having an average diameter greater than about 0.2 micron.

34. The method of claim 16, wherein said sugar-containing material is a fruit juice or fruit juice concentrate.

35. The method of claim 34, further comprising filtering said fruit juice or fruit juice concentrate prior to said treatment to selectively recover proteinaceous materials therefrom.

36. The method of claim 35, wherein said filtration removes particulate material having an average diameter greater than about 0.2 micron.

37. The method of claim 34, wherein said sugar-containing material is apple juice or apply juice concentrate.

38. The method of claim 34, wherein said sugar-containing material is orange juice or orange juice concentrate.

39. Rabbit IgG specifically binds to a proteinaceous component of beet sugar, said proteinaceous component of beet sugar comprising at least one proteinaceous material, found in beet sugar, selected from the group consisting of those proteinaceous materials, found in beet sugar, having a molecular weight, as determined by carrying out electrophoresis on said proteinaceous material and comparing its mobility with that of marker proteins of known molecular weight, of about 61,000 daltons, about 45,000 daltons, about 39,000 daltons, about 36,000 daltons, about 30,000 daltons, about 27,000 daltons, about 21,000 daltons and about 16,000 daltons.

40. The rabbit IgG according to claim 39, wherein said proteinaceous component of beet sugar comprises more than about 50% by weight of amino acids linked by acid labile bonds.

41. The rabbit IgG according to claim 40, wherein said proteinaceous component is rich in alanine, serine, glycine and proline.

42. A test kit for the detection of beet sugar in a sugar-containing material comprising:

a predetermined quantity of a first mammalian IgG specifically binds to a proteinaceous component of beet sugar, said proteinaceous component of beet sugar comprising at least one proteinaceous material, found in beet sugar, selected from the group consisting of those proteinaceous materials, found in beet sugar, having a molecular weight, as determined by carrying out electrophoresis on said proteinaceous material and comparing its mobility with that of marker proteins of known molecular weight, of about 61,000 daltons, about 45,000 daltons, about 39,000 daltons, about 36,000 daltons, about 30,000 daltons, about 27,000 daltons, about 21,000 daltons and about 16,000 daltons; and a predetermined quantity of a labelled second mammalian anti-first mammal IgG.

43. The test kit according to claim 42, wherein said mammalian IgG is rabbit IgG and said labelled second mammalian anti-first mammal IgG is labelled goat anti-rabbit IgG.

44. The test kit according to claim 43, wherein said labelled goat anti-rabbit IgG is goat anti-rabbit IgG-alkaline phosphatase conjugate.

* * * * *